(12) United States Patent  
Surti

(10) Patent No.: US 8,317,820 B2
(45) Date of Patent: Nov. 27, 2012

(54) MEDICAL DEVICE WITH PIVOTABLE JAWS

(75) Inventor: Vihar C. Surti, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 330 days.

(21) Appl. No.: 12/645,004

(22) Filed: Dec. 22, 2009

(65) Prior Publication Data

US 2010/0168787 A1 Jul. 1, 2010

Related U.S. Application Data

(60) Provisional application No. 61/141,934, filed on Dec. 31, 2008.

(51) Int. Cl.
*A61B 17/00* (2006.01)

(52) U.S. Cl. .................................. 606/205

(58) Field of Classification Search ......... 606/205–209, 606/142–146, 180, 227; 227/175.1, 19; 600/218–219, 225; 7/128
See application file for complete search history.

(56) References Cited

U.S. PATENT DOCUMENTS

| | | | |
|---|---|---|---|
| 720,385 A | 2/1903 | Storle | |
| 2,614,445 A * | 10/1952 | Riordan | 81/176.3 |
| 5,029,355 A * | 7/1991 | Thai | 7/118 |
| 5,209,747 A | 5/1993 | Knoepfler | |
| 5,275,615 A | 1/1994 | Rose | |
| 5,586,986 A * | 12/1996 | Hinchliffe | 606/147 |
| 5,797,923 A | 8/1998 | Aiyar et al. | |
| 5,843,098 A * | 12/1998 | Allen et al. | 606/144 |
| 6,358,197 B1 | 3/2002 | Silverman et al. | |
| 7,326,221 B2 | 2/2008 | Sakamoto | |
| 7,601,159 B2 | 10/2009 | Ewers et al. | |
| 7,722,628 B2 | 5/2010 | Stokes et al. | |
| 7,736,372 B2 | 6/2010 | Reydel et al. | |
| 7,736,374 B2 | 6/2010 | Vaughan et al. | |
| 7,744,613 B2 | 6/2010 | Ewers et al. | |
| 7,766,810 B2 | 8/2010 | Ohdaira | |
| 7,776,057 B2 | 8/2010 | Laufer et al. | |
| 7,815,652 B2 | 10/2010 | Messerly et al. | |
| 8,092,489 B2 * | 1/2012 | Ewers et al. | 606/208 |
| 2005/0234296 A1 | 10/2005 | Saadat et al. | |
| 2005/0272977 A1 | 12/2005 | Saadat et al. | |

(Continued)

FOREIGN PATENT DOCUMENTS

CN 202119325 * 1/2012

(Continued)

OTHER PUBLICATIONS www.beveragefactory.com 2008.*

(Continued)

*Primary Examiner* — Gary Jackson
*Assistant Examiner* — Amy Shipley
(74) *Attorney, Agent, or Firm* — Brinks Hofer Gilson & Lione

(57) ABSTRACT

A medical device with pivotable jaws and method of use thereof are disclosed. The device includes a pair of jaw members which are capable of being rotated independently of one another and spaced apart up to about 360°. Various gear arrangements are provided for enabling rotation of the jaws. The jaw members are disposed within a flexible slotted housing when advanced to a target tissue site, and thereafter rotated out of the housing a predetermined amount to contact target tissue.

20 Claims, 4 Drawing Sheets

U.S. PATENT DOCUMENTS

| | | | |
|---|---|---|---|
| 2006/0084886 A1 | 4/2006 | Reydel | |
| 2006/0266161 A1* | 11/2006 | Mulcaire | 81/3.45 |
| 2007/0073185 A1* | 3/2007 | Nakao | 600/564 |
| 2007/0250113 A1 | 10/2007 | Hegeman et al. | |
| 2007/0287993 A1 | 12/2007 | Hinman et al. | |
| 2008/0147113 A1 | 6/2008 | Nobis et al. | |
| 2008/0171907 A1 | 7/2008 | Long et al. | |
| 2008/0228199 A1 | 9/2008 | Cropper et al. | |
| 2008/0228202 A1 | 9/2008 | Cropper et al. | |
| 2008/0234703 A1 | 9/2008 | Cropper et al. | |
| 2008/0234705 A1 | 9/2008 | Cropper et al. | |
| 2008/0255427 A1 | 10/2008 | Satake et al. | |
| 2008/0262539 A1 | 10/2008 | Ewers et al. | |
| 2008/0269557 A1 | 10/2008 | Marescaux et al. | |
| 2008/0269566 A1 | 10/2008 | Measamer | |
| 2008/0275441 A1 | 11/2008 | Aue | |
| 2008/0287963 A1 | 11/2008 | Rogers et al. | |
| 2008/0294178 A1 | 11/2008 | Kortenbach et al. | |
| 2008/0300461 A1 | 12/2008 | Shaw et al. | |
| 2008/0300624 A1 | 12/2008 | Schwemberger et al. | |
| 2009/0005638 A1 | 1/2009 | Zwolinski | |
| 2009/0018602 A1 | 1/2009 | Mitelberg et al. | |
| 2009/0062792 A1 | 3/2009 | Vakharia et al. | |
| 2009/0138006 A1* | 5/2009 | Bales et al. | 606/33 |
| 2009/0143794 A1 | 6/2009 | Conlon et al. | |
| 2009/0192344 A1 | 7/2009 | Bakos et al. | |
| 2009/0221915 A1 | 9/2009 | Voegele et al. | |
| 2009/0299385 A1 | 12/2009 | Stefanchik et al. | |
| 2009/0306683 A1 | 12/2009 | Zwolinski et al. | |
| 2009/0306686 A1 | 12/2009 | Ohdaira | |
| 2009/0326518 A1 | 12/2009 | Rabin | |
| 2009/0326578 A1 | 12/2009 | Ewers et al. | |
| 2010/0042115 A1 | 2/2010 | Saadar et al. | |
| 2010/0057078 A1 | 3/2010 | Arts et al. | |
| 2010/0130817 A1 | 5/2010 | Conlon | |
| 2010/0179540 A1 | 7/2010 | Marczyk et al. | |
| 2010/0198149 A1 | 8/2010 | Fox | |
| 2010/0198248 A1 | 8/2010 | Vakharia | |
| 2010/0211086 A1 | 8/2010 | Ewers et al. | |
| 2010/0217151 A1 | 8/2010 | Gostout et al. | |
| 2010/0249498 A1 | 9/2010 | Wingardner et al. | |
| 2010/0249700 A1 | 9/2010 | Spivey | |
| 2010/0249808 A1 | 9/2010 | Harada et al. | |

FOREIGN PATENT DOCUMENTS

| | | | |
|---|---|---|---|
| DE | 102006003548 | * | 1/2006 |
| DE | 102006003548 | | 8/2007 |

OTHER PUBLICATIONS

International Search Report/Written Opinion for PCT/US2009/069270 (May 17, 2010).

* cited by examiner

MEDICAL DEVICE WITH PIVOTABLE JAWS

CROSS-REFERENCE

This application claims the benefit of U.S. Provisional Application Ser. No. 61/141,934 filed on Dec. 31, 2008, entitled "MEDICAL DEVICE WITH PIVOTABLE JAWS," the entire contents of which are incorporated herein by reference.

BACKGROUND

Medical devices for engaging tissue are used during several types of procedures, including open surgery, laparoscopic surgery, endoscopic surgery, or transluminal surgery. Such devices include graspers, snares, baskets and the like. One common type of tissue engagement medical device that is available for endoluminal engagement of body tissue is forceps. Conventional forceps includes a pair of hinged jaws located at a distal end of a tubular housing. The hinged jaws are commonly activated using a typical actuator such as a push/pull wire mechanism, in which an actuating element such as a wire extends through the tubular housing to connect to the jaws via a mechanical linkage, which in turn drives the jaws between a closed position and a "V" shaped open position. Closing the jaws from the "V" shaped open position causes the jaws to catch on, pinch, or entrap tissue during a procedure. The extent to which the jaws open is typically limited by the mechanical linkage to the "V" shape; usually the jaws are separated by about 90° in their open position.

SUMMARY

The invention may include any of the following aspects in various combinations and may also include any other aspect described below in the written description or in the attached drawings.

In a first aspect, a medical device is provided that improves the effectiveness of the jaws in procedures where a wider angular opening of the jaws is necessary for access and grasping of target tissue. The device comprises a drive gear, a first elongate arm, and a second elongate arm. The first elongate arm comprises a first jaw member and a first gear end. The first gear end is intermeshed with the drive gear. The second elongate arm comprises a second jaw member and a second gear end. The second gear end is intermeshed with the drive gear. The first elongate arm and the second elongate arm are each pivotable about the first gear end and the second gear end, respectively. Each of the first elongate arm and the second elongate arm is pivotable between a first closed position and a second open position. The first jaw member and the second jaw are disposed adjacent each other in the first closed position, while the first jaw member and the second jaw member are spaced apart by an angle of about 360° in the second position.

In a second aspect, a medical device is provided. The medical device comprises a drive gear comprising an elongated rack having a longitudinal length. The drive gear further comprises a first gear surface and a second gear surface being opposed to the first gear surface. A plurality of first ribs laterally protrude away from the first gear surface of the elongate rack along the longitudinal length of the drive gear. The plurality of first ribs define a first plurality of slots therebetween, A plurality of second ribs laterally protrude away from the second gear surface of the elongate rack along the longitudinal length of the drive gear. The plurality of second ribs define a second plurality of slots therebetween. The device also includes a first elongate arm and a second elongate arm. The first elongate arm comprises a first jaw member and a first gear end, the first gear end comprising a first plurality of teeth pivotally connected within the distal end of the housing at a first pivot point, wherein the first plurality of teeth are engaged with the plurality of the first slots of the drive gear. The second elongate member comprises a second jaw member and a second gear end, the second gear end comprising a second plurality of teeth pivotally connected within the distal end of the housing at a second pivot point, the second plurality of teeth engaged with the plurality of the second slots of the drive gear. A housing is also provided. The housing comprises a proximal end, a distal end, and at least one opening extending between the proximal end and the distal end, wherein the housing receives the first and the second elongate arms in a fully open configuration to substantially enclose the arms.

In a third aspect, a method for grasping an object is provided comprising the following steps. A medical device is provided. The device comprises a first elongate arm disposed within a housing and comprises a first jaw member and a first gear end. The first gear end is intermeshed with a drive gear at the distal end of the housing. A second elongate arm is disposed within the housing and comprises a second jaw member and a second gear end intermeshed with the drive gear at the distal end of the housing. The first elongate arm and the second elongate arm are independently pivotable with respect to each other about the first and the second gear ends respectively. Rotation of the first and the second elongate arms controls a spacing between the first jaw member and the second jaw member from about 0° to about 360°. The medical device is advanced to the object, e.g. through a bodily lumen to a target tissue site, with the first jaw member and the second jaw member in a fully open configuration being substantially enclosed within the housing, preferably in a substantially parallel arrangement at about 360° relative to each other. The drive gear is pulled in a proximal direction so as to cause engagement of the drive gear with the first gear end and the second gear end, thereby causing rotation of the first elongate arm in a clockwise direction about the first gear end from a bottom opening of the housing, and rotation of the second elongate arm in a counterclockwise direction about the second gear end from a top opening of the housing. The movement of the arms closes the first and the second jaw members around the object to grasp and retain the object.

BRIEF DESCRIPTION OF SEVERAL VIEWS OF THE DRAWINGS

The invention may be more fully understood by reading the following description in conjunction with the drawings, in which.

DETAILED DESCRIPTION

The terms "proximal" and "distal" as used herein are intended to have a reference point relative to the user. Specifically, throughout the specification, the terms "distal" and "distally" shall denote a position, direction, or orientation that is generally away from the user, and the terms "proximal" and "proximally" shall denote a position, direction, or orientation that is generally towards the user.

Figure 1:
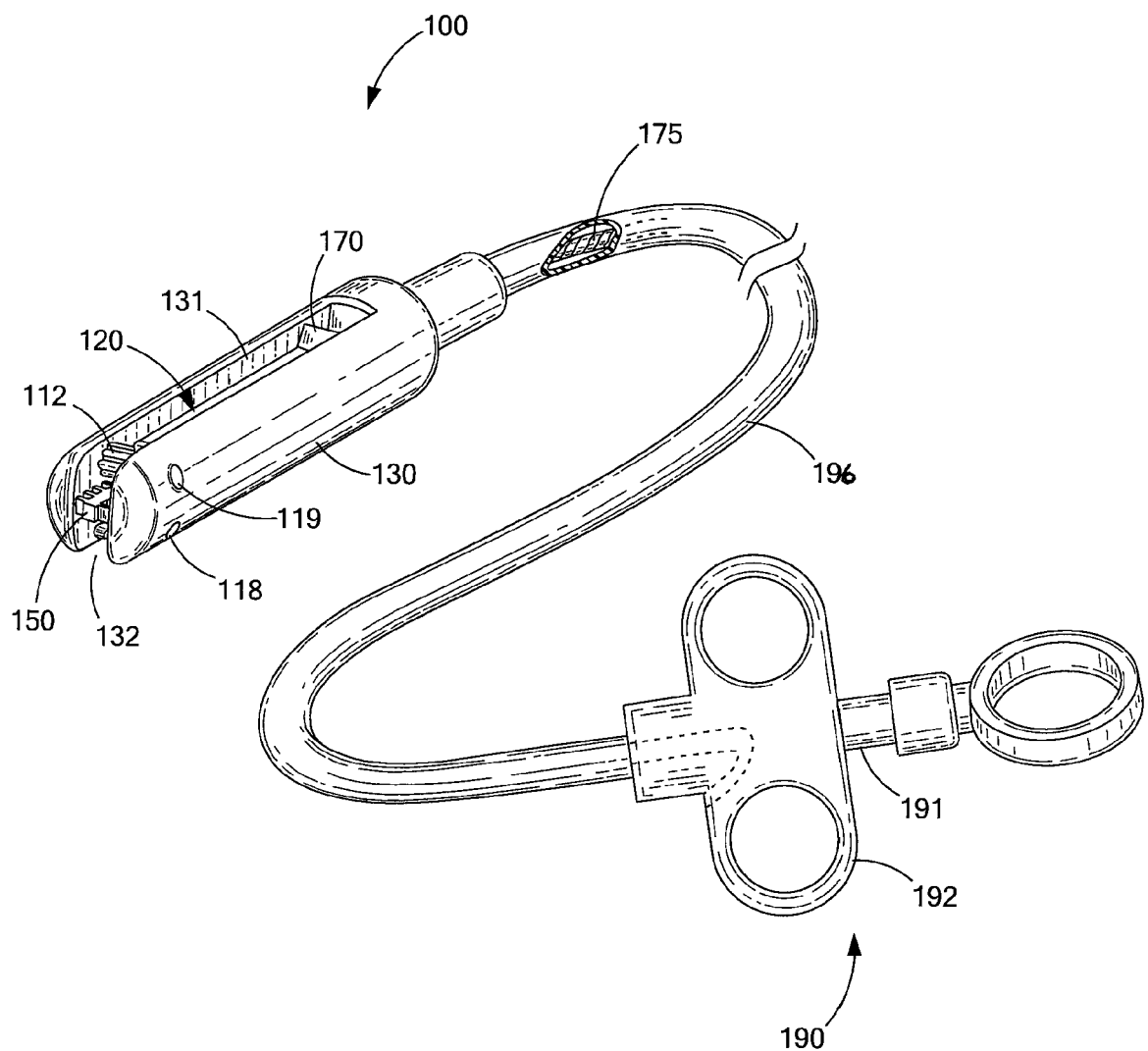
FIG. 1 shows a perspective view of a medical device with pivotable jaws having elongate members disposed within a flexible housing, the elongate members being in a closed position.

An exemplary medical device with pivotable jaws is shown in FIG. 1. FIG. 1 shows a perspective view of a medical device 100 having a first elongate arm 110 and a second elongate arm 120 both of which are disposed within a slotted housing 130 having an opening 131 sized to substantially enclose the arms 110 and 120. The first elongate arm 110 and the second elongate arm 120 are shown substantially parallel to each other in the fully open position, which is shown more clearly in FIG. 2a. As will be explained in greater detail, the device 100 is designed to allow rotation of the arms 110 and 120 and their corresponding jaw members 160 and 170 from about 0° to about 180°, thereby enabling a separation angle between the jaw members 160 and 170 to range from 0° to about 360°. The terms "about" or "generally" as used herein with reference to relative spacing, generally includes a deviation of plus or minus 15°. For example, in the fully open position of the arms 110, 120 and jaws 160, 170 they may be only spaced apart 300°, yet be substantially or entirely contained within the housing 130.

Figure 2A:
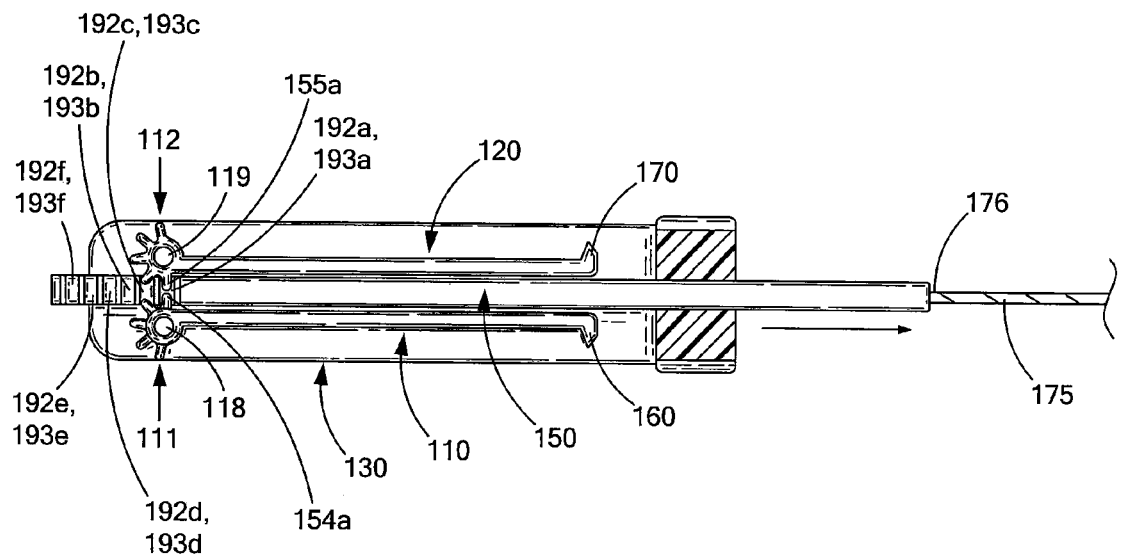
FIG. 2A shows a partial cross-sectional view of a distal end of the device of FIG. 1.

The first elongate arm 110 in the fully open position is disposed along the bottom portion of opening 131 of the slotted housing 130. The first elongate arm 110 includes a first gear end 111 that is pivotally connected by a first pivot pin 118 along the distal end of the slotted housing 130. The first gear end 111 remains stationary as it intermeshes with a drive gear 150, which is disposed between the first gear end 111 and the second gear end 112, as seen more clearly in FIG. 2A. The first elongate arm 110 further includes a first jaw member 160, which is shown disposed within the housing 130 along the proximal end thereof (FIG. 2a). The jaw member 160 is shown positioned along an end opposite to the first gear end 111.

The second elongate arm 120 in the fully open position is disposed along the top portion of opening 131 of the slotted housing 130, as can be seen in FIG. 1 and FIG. 2a. FIG. 1 shows that the second elongate arm 120 includes a second gear end 112, which is pivotally connected by a second pivot pin 119 along the distal end of the slotted housing 130. The second gear end 112 remains stationary as it intermeshes with the drive gear 150. The second elongate arm 120 includes a second jaw member 170, which can be seen in FIG. 1 to be disposed within the flexible housing 130 along the proximal end thereof. The second jaw member 170 is shown positioned along an end opposite to the second gear end 112.

FIG. 2A shows the first elongate arm 110 and the second elongate arm 120 in the fully open position. The fully open position is defined as the elongate arms 110 and 120 positioned substantially parallel to each other within a proximal end of the flexible slotted housing 130 such that the first and second jaw members 160 and 170 are spaced apart about 360° relative to each other. Similarly, the fully closed position, as shown in FIG. 2c, is defined as the elongate arms 110 and 120 positioned substantially parallel to each other and distally of the distal end of the housing 130 such that the first and second jaw members 160 and 170 are spaced at 0° relative to each other. The mechanism by which the elongate arms 110 and 120 rotate from the fully open position (FIG. 2A) to the fully closed position (FIG. 2C) enables a wider range of angular motion of arms 110 and 120 relative to conventional medical devices having rotatable members, such as, for example, grasping elements, cutting elements, or biopsy elements. The first elongate arm 110 and the second elongate arm 120 are configured to rotate independently of each other. The first elongate arm 110 is adapted to rotate 180° clockwise relative to a drive gear 150 (FIG. 2b) and about pivot pin 118. The second elongate arm 120 is adapted to rotate 180 degrees counterclockwise relative to the drive gear 150 (FIG. 2b) and about pivot pin 119. 360° separation relative to each of the arms 110 and 120 and their corresponding jaw members 160 and 170 is possible with device 100 (FIG. 2c). The rotation of the arms 110 and 120 enables controlled spacing of the jaws 160 and 170 from about 0° to about 360° during a procedure that involves grasping tissue.

FIG. 1 shows that the slotted housing 130 contains an opening 131 that is sufficiently sized to receive the first elongate arm 110 and the second elongate arm 120 therewithin. The distal end of the housing 130 has an opening 132 which allows the first and the second elongate arms 110 and 120 to pivot from the fully open position (FIG. 2a) to the fully closed position (FIG. 2c).

Figure 2B:
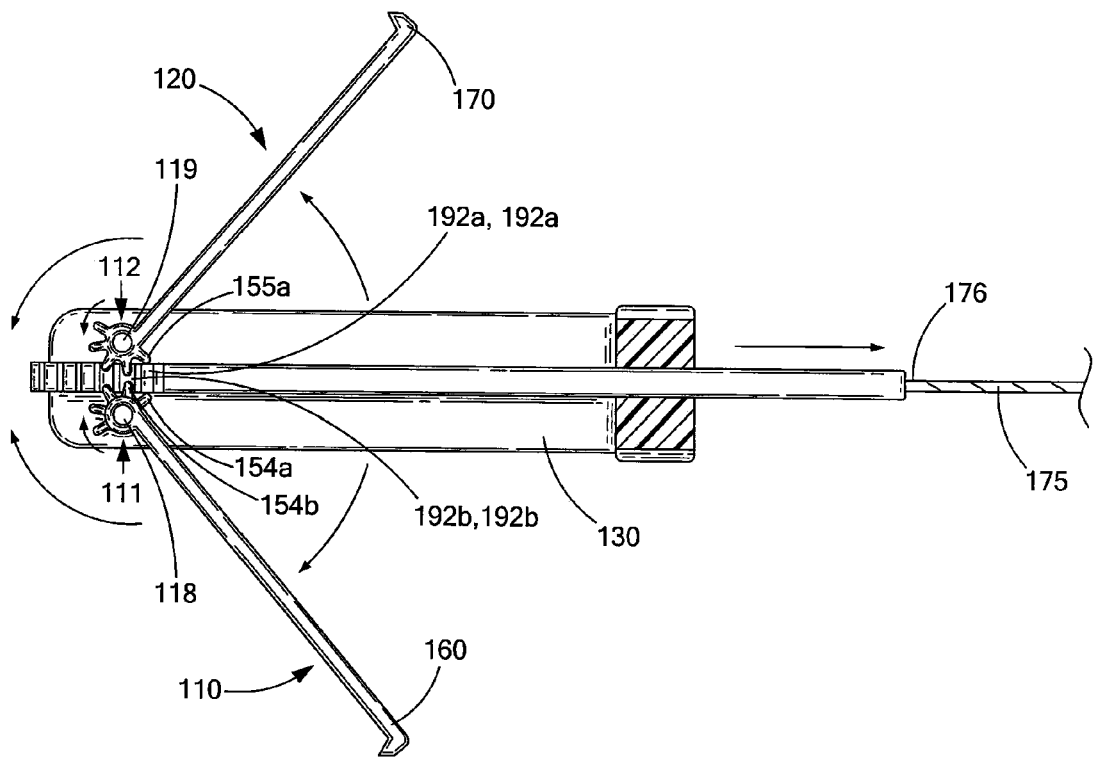
FIG. 2B shows the medical device with the first elongate member rotated 45° in a clockwise direction from a bottom opening of the housing and the second elongate member rotated 45° in a counterclockwise direction from a top opening of the housing.
Figure 2C:
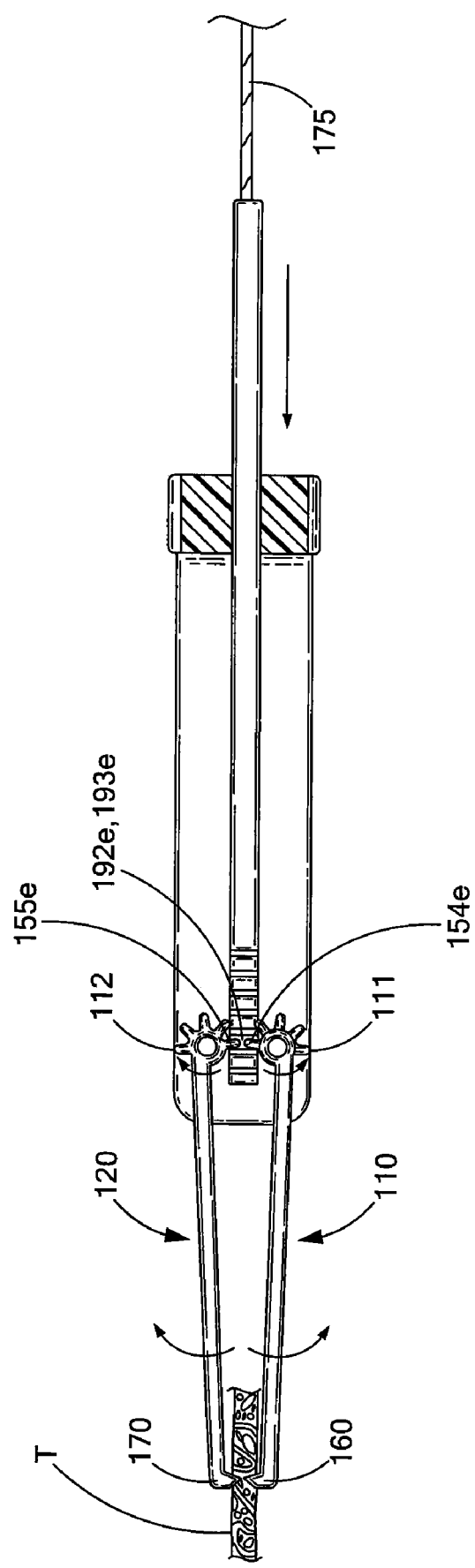
FIG. 2C shows the medical device of FIG. 1 in which the elongate members have rotated to their fully closed position with the corresponding jaw members of elongate members disposed adjacent to each other.
Figure 3:
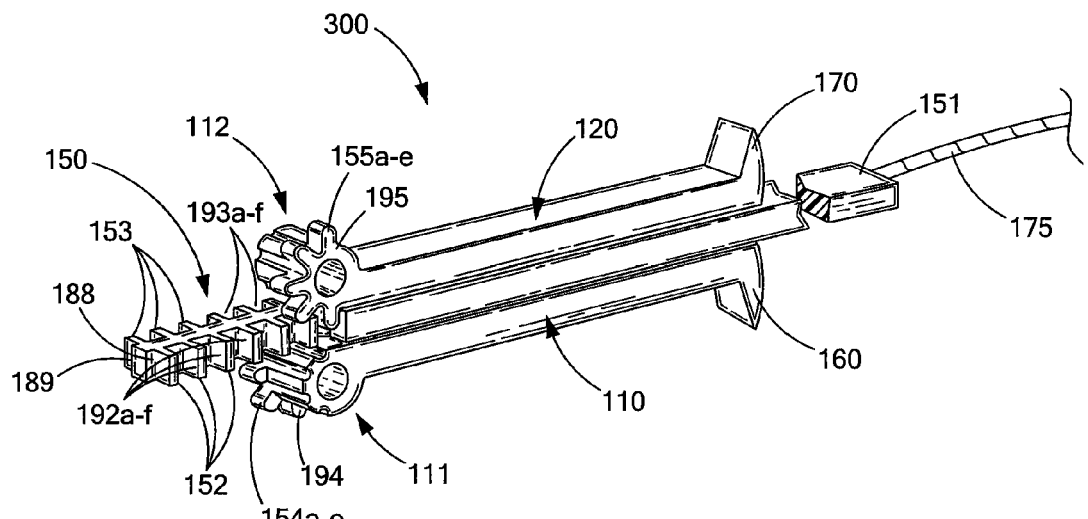
FIG. 3 shows a gear arrangement that may be utilized in the medical device of FIG. 1.

A detailed view of the gear arrangement 300 used in FIG. 1 and FIGS. 2a-2c is shown in FIG. 3. The gear arrangement 300 includes a drive gear 150 intermeshed with the first gear end 111 and the second gear end 112. The drive gear 150 includes an elongated rack 151 having a first gear surface 188 and a second gear surface 189. A predetermined distal portion of the elongated rack 151 includes multiple first ribs 152 which laterally extend or protrude away from the first surface 188. A predetermined distal portion of elongate rack 151 also includes multiple second ribs 153 which laterally extend or protrude away from a second surface 189 of the elongate rack 151. The spacing between adjacent first ribs 152 creates multiple first slots 192a-f therebetween, which are sized to receive a corresponding first set of teeth 154a-e contained along the outer surface of the first gear end 111. 192a refers to the most proximal first slot, and 192f refers to the most distal first slot. The spacing between adjacent second ribs 153 creates multiple second slots 193a-f therebetween, which are sized to receive a corresponding second set of teeth 155a-e contained along the outer surface of the second gear end 112. Note that the second slots 193a-f are positioned on the other side of the elongate rack 151 along back surface 189 (FIG. 3) and therefore are not visible in the cross sectional views of FIGS. 2a-2c. Similar designation is used in which 193a refers to the most proximal second slot, and 193f refers to the most distal second slot. Multiple second slots 193a-f along the first surface 188 of elongate rack 151 are aligned with multiple first slots 192a-f along with second surface 189 of the elongate rack 151. FIG. 3 shows that the first set of teeth 154a-e extend only along face 194 of the first gear end 111. The second set of teeth 155a-e extend only along face 195 of the second gear end 112. Faces 194 and 195 are oriented opposite and away from each other to enable drive gear 150 to sufficiently engage with both the first set of teeth 154 of first gear end 111 and the second set of teeth 155 of the second gear end 112. In other words, the teeth 154 and 155 may be longer than conventional teeth in gear arrangements to enhance mesh engagement of the teeth 154a-e and 155a-e within their respective slots 192a-f and 193a-f along the drive gear 150. The meshed engagement of teeth 154a-e and 155a-e within their respective slots 192a-f and 193a-f is designed to be possible even when the overall profile of the device 100 must be substantially reduced to about 20 Fr or smaller, as is generally required for endoscopic procedures. On the contrary, conventional gear arrangements at such small diameters may need to utilize a drive gear having relatively shallow vertical indentations or grooves that engage with shorter teeth along the gear ends of the elongate arms. Such a gear design may be problematic as slippage between the teeth and the vertical grooves of the drive gear may occur due to the need to reduce the overall profile of the device. Accordingly, the above described gear arrangement 300 may be significantly less prone to slippage as the overall profile of the device is required to be reduced.

Variations to the above described gear arrangement 300 are contemplated. The gear arrangement 300 described above may be modified such that the rack 151 may only include a single set of laterally extended slots shared by both sets of teeth 154a-e and 155a-e. In particular, a single set of ribs may extend along one of the surfaces 188 and 189 of rack 151. Lateral slots would be created between the ribs, and the slots may be sized to receive both sets of teeth 154a-e and 155a-e.

The mechanism by which the first elongate arm 110 and the second elongate arm 120 rotate will be explained in conjunction with FIGS. 2a-2c. FIG. 2a shows that first elongate arm 110 and the second elongate arm 120 are in the fully open position within the flexible housing 130. In particular, the outermost tooth 154a of the first gear end 111 is shown engaged with corresponding proximal-most slot 192a. The outermost tooth 155a of second gear end 112 is shown engaged with corresponding proximal-most slot 193a of drive gear 150. The configuration of tooth 154a with corresponding slot 192a and tooth 155a with corresponding slot 193a enables the first and the second jaw members 160 and 170 to be oriented at 360° relative to each other within the proximal end of the flexible housing 130 (FIG. 2a).

A control handle 190 as shown in FIG. 1 may be used to actuate the drive gear 150. In particular, a distal end of a drive wire 175 connects to a proximal end 176 of drive gear 150 (FIG. 2a). Drive wire 175 is actuated by control handle 190. A proximal end of the drive wire 175 connects to the control handle 190. It should be understood that other configurations of control handle 190 can be employed to actuate drive wire 175. For example, the control handle 190 may be a scissors-type handle, a pin vise, or any other conventional handle suitable for moving a drive wire 175 relative to a sheath 196. Although the term "wire" is used to describe the elongate control member 175, the member may be formed from any material (i.e. metals, alloys, plastics, ceramics) and includes any elongate structure capable of longitudinal force transmission over typical endoscope and/or laparoscopic distances, including single filament or multifilament wires, stylets, tubes, catheters, plastic rods or strands, and the like.

The sheath 196 may be a tubular member. The sheath 196 has a lumen which houses a drive wire 175, the drive wire 175 connecting at its distal end to the drive gear 150 and at its proximal end to a control handle 190. The sheath 196 allows connection of the drive wire 175 from the proximal end of the drive gear 150 to the spool 192, which will be explained in greater detail below. The distal end of sheath 196 is affixed to the proximal end of housing 130, and the proximal end of sheath 196 is affixed to control handle 190. The sheaths 196 may range in length from about 160 cm to about 220 cm. The sheath 196 is a flexible tubular member and may be formed from any semi-rigid polymer. For example, the sheath 196 can be formed from polyurethane, polyethylene, tetrafluoro-ethylene, polytetrafluoroethylene, perfluoalkoxl, fluorinated ethylene propylene, or the like. Other structures that can house the drive wire 175 are contemplated. For example, the sheath 196 may be a wound coiled spring.

Control handle 190 includes a stem 191 and a spool 192. Stem 191 includes a lumen through which drive wire 175 is disposed therewithin. Spool 192 is slidably engaged with stem 191, and spool 192 is operably connected to the drive wire 175. Spool 192 is provided with a range of slidable motion along stem 191. Thus, movement of the spool 192 in a proximal direction relative to the stem 191 causes drive wire 175 to proximally move relative to the sheath 196. The movement causes a tensile force to be transmitted to the drive wire 175. The drive wire 175 subsequently exerts a pulling force on the proximal end 176 of the drive gear 150 to cause the drive gear 150 to linearly move in the proximal direction, as indicated by the arrow in FIG. 2a. Linear movement of the drive gear 150 in the proximal direction causes first gear end 111 to rotate about pivot pin 118 in a clockwise direction, as shown by the arrow about first gear end 111, thereby causing first elongate member 110 to rotate in a clockwise direction. The linear movement of the drive gear 150 in the proximal direction also causes the second gear end 112 to rotate about pivot pin 119 in a counterclockwise direction, as shown by the arrow about second gear end 112, thereby causing second elongate member 120 to rotate in a counterclockwise direction.

FIG. 2b shows that the first gear end 111 has rotated clockwise a sufficient amount to disengage the outermost spoke 154a of the first set of teeth 154 from slot 192a such that first spoke 154b engages within corresponding first slot 192b. Second gear end 112 has rotated counterclockwise a sufficient amount to disengage the outermost second spoke 155a from slot 193a such that second spoke 155b engages within corresponding slot 193b. FIG. 2b shows that during the engagement, the teeth 154 and 155 of the first and second gear ends 111 and 112 are projected substantially vertically with the corresponding lateral slots 192 and 193 of the rack 151. The net result is that the first elongate arm 110 has rotated from the bottom of housing 130 approximately 45 degrees in a clockwise direction, and the second elongate arm 120 has rotated from the top of housing 130 approximately 45 degrees in a counterclockwise direction, as shown in FIG. 2b.

FIG. 2b shows that the drive gear 150 continues to be pulled in a proximal direction which will cause the first gear end 111 to further rotate in a clockwise direction such that first spoke 154b is disengaged from corresponding first slot 192b and thereafter first spoke 154c of first gear end 111 engages within corresponding slot 192c of drive gear 150. Such movement causes the first elongate arm to move an additional 45 degrees in the clockwise direction, thereby creating about 90° total movement from the fully closed position of FIG. 2a. Similarly, pulling drive gear 150 in the proximal direction causes the second gear end 112 to further rotate in a counterclockwise direction such that the second spoke 155b is disengaged from corresponding second slot 193b and thereafter second spoke 155c of second gear end 112 engages within corresponding slot 193c of the drive gear 150. This movement causes the second elongate arm 120 to move an additional 45° in the counterclockwise direction, thereby creating about 90° total movement from the fully open position of FIG. 2a.

The handle 190 may be pulled in the proximal direction until the first and the second elongate arms 110 and 120 have rotated 180° such that jaw members 160 and 170 are fully closed, as shown in FIG. 2c. The tip of jaw member 160 is in contact with the tip of jaw member 170. FIG. 2c shows that the first elongate arm 110 has been rotated 180 degrees in the clockwise direction from the open position of FIG. 2a. The second elongate arm 120 has been rotated 180° in the counterclockwise direction from the open position of FIG. 2a. The gear arrangement 300 in the fully closed position shows that the first spoke 154e is engaged within corresponding first slot 192e, and the second spoke 155e is engaged within corresponding second slot 193e. Such a wider range of movement of the jaw members 160 and 170 may enable the jaw members 160 and 170 to access and capture target tissue that may not typically be possible with conventional jaw members, which can only undergo a limited range of motion. Additionally, the ability for elongate arms 110 and 120 to be extended in the fully open position FIG. 2c and be separated 360° from each other may enable a larger amount of tissue to be captured compared to conventional medical jaw devices.

In the above described embodiment of FIGS. 2a-2c, the first set of teeth and the second set of teeth were not required to extend completely around their respective gear ends 111 and 112, as each meshed engagement and subsequent disengagement of a single spoke with a corresponding slot created 45 degrees of rotational movement. As a result, five teeth were required to create about 180° movement of the first and the second elongate members 110 and 120. More than 5 teeth may be used in the gear arrangement 300 to decrease the incremental rotation created from meshed engagement-disengagement of a spoke and corresponding slot. Alternatively, less than 5 teeth may be used to increase the incremental rotation. The exact number of teeth around each of the gears may depend, in part, on the type of procedure into which device 100 is being utilized and the size constrains associated with such a procedure. Preferably, a sufficient number of teeth and corresponding slots are provided so as to allow about 180° movement of the first and the second elongate arms 110 and 120.

It should be understood that the above described mechanism for opening and closing jaw members 160 and 170 can be used for any type of jaw member, including but not limited to graspers, biopsy cups, scrapers, and scissors. In one example, the jaw mechanism and design as described above may be used for clips having detachable distal ends which may remain in a patient and mechanically maintain compression on a target structure after the particular procedure is completed. Inner surfaces of the jaw members 160 and 170 may include serrated features for enhancing the ability to severe tissue. The exact structure of the jaws members 160 and 170 may be dependent upon a variety of factors, including the particular application for the device 100.

Figure 4:
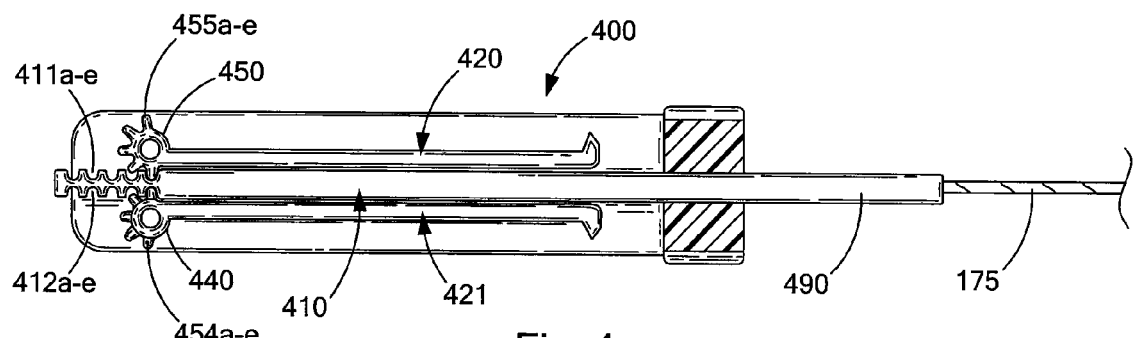
FIG. 4 shows another gear arrangement that may be utilized in the device of FIG. 1.

Additional variations to the gear arrangement 300 (FIG. 3) described in conjunction with FIGS. 2a-2c are also contemplated. FIG. 4 shows an example of an alternative gear arrangement 400. The central drive gear 410 includes a first set of grooves 412 a-e which engage with corresponding teeth 454a-e of a first gear 440. The drive gear 410 also includes a second set of grooves 411 a-e which engage with corresponding teeth 455a-e of a second gear 450. Unlike the rectangular slots 192a-f and 193a-f which are created along opposing sides of the elongate rack 151 (FIG. 3), the grooves 411a-e are created along a top surface of an elongate member 490 of the drive gear 410, and the grooves 412a-e are created along a bottom surface of elongate member 490. In the example of FIG. 4, each of five teeth 454a-e engage and subsequently disengage with corresponding grooves 412a-e, and each of five teeth 455a-e engage and subsequently disengage with corresponding grooves 411 a-e. Such meshed arrangement allows first elongate arm 421 to rotate clockwise from the bottom opening of housing 130 and second elongate arm 420 to rotate counterclockwise from the top opening of housing 130. Each of the elongate arms 420 and 421 are capable of rotating 180 degrees from their open position as shown in FIG. 4.

Figure 5:
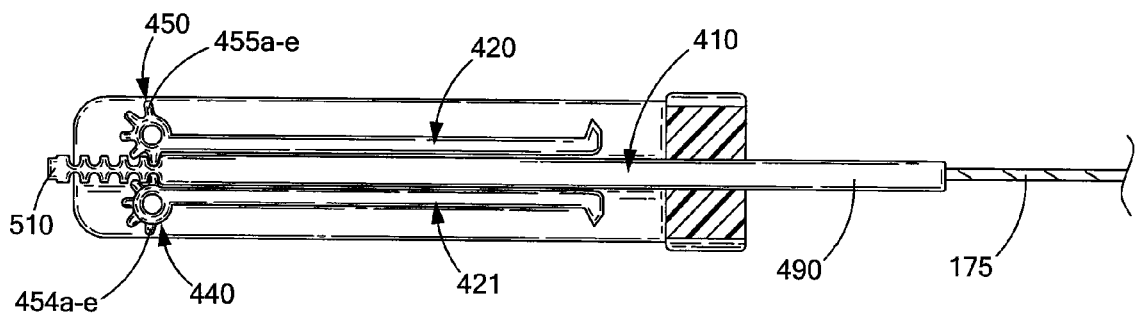
FIG. 5 shows yet another gear arrangement in which the drive gear comprises a stopper element placed distally of the distal-most groove of the drive gear, the stopper element preventing disengagement of the drive gear from both gear ends of the elongate members during proximal pulling of the drive gear.

FIG. 5 shows that a stopper element 510 may be disposed along the distal end of the drive gear 410 to prevent the drive gear 410 from proximally moving beyond the first gear end 111 and the second gear end 112 so as to disengage therefrom. The stopper element 510 is shown to have a length greater than the spacing between adjacent teeth 454a-e of first elongate arm 421 and adjacent teeth 455a-e of second elongate arm 420, thereby preventing stopper element 510 from engaging into the openings defined by the spacing of adjacent teeth 454a-e and 455a-e. Accordingly, no further rotation of the first gear end 440 and the second gear end 450 may be possible when the stopper element 510 is abutted against the first and the second gear ends 440 and 450. Preferably, the stopper element 510 is placed distally of the most distal slot or groove of the drive gear 150 along the distal portion of the elongate member 490.

The flexible slotted housing 130 preferably has a longitudinal length sufficient to house and substantially the first and the second elongate arms 110 and 120 in their fully open position as shown in FIGS. 1, 2, 4, and 5. Specifically, the housing 130 preferably has a top and bottom opening 131 which is sized to receive elongate members 110 and 120. The distal end of the housing 130 also contains an opening 132 to enable a complete range of rotation of the members 110 and 120. The housing 130 is preferably made from any flexible polymeric material known in the art. As a result, the flexibility of the housing 130 may allow the device 100 to be navigated through an accessory channel of an endoscope and tortuous body lumens. Additionally, because the elongate members 110 and 120 and corresponding jaw members 160 and 170 are completely embedded within a flexible slotted housing 130 during advancement to a target tissue site, the embodiments described herein may not be limited by a maximum length of elongate members 110 and 120, as may be likely with conventional medical devices having jaws. Such conventional medical devices tend to have elongate members which are too rigid to traverse tortuous bends as well an accessory channel of an endoscope. Accordingly, the length of such conventional elongate members often needs to be shortened to facilitate advancement through tortuous bends. The present embodiments as described herein, however, may enable longer elongate members 110 and 120 to be introduced into the accessory channel of the endoscope and subsequent tortuous body lumens. The longitudinal length of elongate members 110 and 120 as contemplated herein may be about 0.5 inches (12.7 millimeters) or greater.

One exemplary method of using the device 100 involves an endoscopic procedure. An endoscope is advanced through an esophagus and into the gastrointestinal tract of a patient. The device 100 is introduced into an accessory channel of an endoscope in which the elongate members 110 and 120 are in their fully open position as shown in FIG. 1, the jaw members 160 and 170 being spaced apart about 360°. The orientation of FIG. 1 creates an overall reduced lateral profile of device 100 during advancement through accessory channel of the endoscope. The proximal end of the handle assembly 190 is advanced beyond a distal end of the accessory channel towards a target tissue site T (FIG. 2C) so as to advance device 100 through a bodily lumen to the target tissue site while the first and the second elongate members 110 and 120 remain in their open position (FIG. 1). Having reached the target tissue site, the first elongate arm 110 with jaw member 160 is rotated from the bottom opening 131 of housing 130 in a clockwise direction and the second elongate arm 120 with jaw member 170 is rotated from the top opening of housing 130 in a counterclockwise direction. Such rotational movement is shown in FIG. 2b. The rotational movement is preferably achieved utilizing the gear arrangement 300 discussed above in conjunction with FIG. 3. Depending on the sizes of the body lumen and the location of target tissue, the arms 110 and 120 may be rotated in the fully closed position, as shown in FIG. 2c. In this particular example, the elongate members 110 and 120 are rotated about 180° in the configuration of FIG. 2c such that corresponding jaw members 110 and 120 may close around the tissue to grasp the target tissue. The optional stopper element 510 (FIG. 5) may be utilized to prevent the drive gear 150 from being proximally pulled back beyond the first and second gear ends 111 and 112, thereby preventing disengagement of drive gear 150 from the gear ends 111 and 112.

Having grasped the target tissue, the drive gear 150 is pushed in the distal direction as shown by the arrow in FIG. 2c. Movement of drive gear 150 in the distal direction causes meshed engagement of the drive gear 150 with the first gear end 111 so as to rotate the first gear end 111 and the first elongate arm 110 in the counterclockwise direction, as shown by the arrow about arm 110 in FIG. 2c. The drive gear 150 is also in meshed engagement with the second gear end 112 so as to rotate second gear end 112 and second elongate arm 111 in the clockwise direction, as shown by the arrow about arm 120 in FIG. 2c. The drive gear 150 may continue to be pushed in the distal direction until first elongate arm 110 and second elongate arm 120 are rotated back into the fully open position, as shown in FIG. 2a.

Although not shown, an additional proximal stopper element similar to distal stopper element 510 (FIG. 5) may be disposed proximal of the most proximal slot or groove of the drive gear 150 (FIG. 5) along the distal portion of the elongate rack 151. The proximal stopper element would have a length greater than the spacing between adjacent teeth 454a-e of first elongate arm 421 and adjacent teeth 455a-e of second elongate arm 420 (FIG. 5) to prevent the proximal stopper element 510 from engaging into the openings defined by spacing of adjacent teeth 454a-e and 455a-e. Accordingly, no further rotation of the first gear end 111 and the second gear end 112 may be possible when the proximal stopper element is abutted against the first and the second gear ends 111 and 112. Having a pair of stopper elements in such a configuration along elongate rack 151 of drive gear 150 reduces the risk of disengagement of the drive gear 150 from the first and second gear ends 111 and 112 during either proximal pulling of drive gear 150 (i.e., to open the arms 110 and 120 out from housing 130) or distal pushing of drive gear 150 (i.e., to close the arms 110 and 120 into housing 130).

As can be seen, unlike conventional grasping medical devices, the above described method of use involves delivering the device 100 with the elongate members 110 and 120 positioned in a fully open configuration (FIG. 2a) and completely disposed within the housing 130 during delivery. The sharp jaws 160 and 170 in their fully open configuration during delivery remain protected by being encapsulated within housing 130. Because conventional devices allow the jaw member to remain exposed, there may be a greater risk of the exposed jaw inadvertently contacting tissue that causes trauma to the patient during a procedure. Such risk is significantly eliminated with the above described device 100.

It will be recognized by those skilled in the art that, while the devices and methods described above generally include operating on tissue through an internal bodily lumen, it will be recognized that the systems, devices and methods may be used on any object (e.g. to retrieve small pieces from hard to reach places, such as a lost ring in a drain or other household plumbing) or on any layer of material (e.g. fabrics, cloth, polymers, elastomers, plastics and rubber) that may or may not be associated with a human or animal body and a bodily lumen. For example, the systems, devices and methods can find use in laboratory and industrial settings for manipulating one or more layers of material that may or may not find application to the human or animal body.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

The invention claimed is:

1. A medical device, comprising:
   a housing having a proximal end and distal end and at least one opening extending between the proximal end and the distal end, the housing defining a longitudinal axis extending between the proximal and distal ends;
   a drive gear moveable relative to the housing;
   an elongate control member having a distal end connected to the drive gear for sliding the drive gear longitudinally;
   a first elongate arm comprising a first jaw member and a first gear end, the first gear end intermeshed with the drive gear and pivotally attached to the housing; and
   a second elongate arm comprising a second jaw member and a second gear end, the second gear end intermeshed with the drive gear and pivotally attached to the housing, the second elongate arm disposed opposite to the first elongate arm;
   wherein the first elongate arm and the second elongate arm are pivotable between a first closed position and a second open position, motion of the drive gear driving the pivoting of the first and second elongate arms between the first closed position and the second open position, the first jaw member and the second jaw member being disposed adjacent each other and distal to the housing in the first closed position, the first jaw member and the second jaw member rotated away from each other and received within the at least one opening to entirely enclose the arms in the second open position, each of the first and second elongate arms rotating about 180° between the first closed position and the second open position.

2. The medical device of claim 1, wherein the drive gear is entirely contained within the housing in the second open position.

3. The medical device of claim 1, wherein a distal end of the drive gear defines a stopper element that does not mesh with the first and second gear ends.

4. The medical device of claim 1, wherein an arced path from the first elongate arm to the second elongate.

5. The medical device of claim 4, the first gear end comprising a first curved gear surface comprising a first plurality of teeth that extend along the first curved surface about 180°, and the second gear end comprising a second curved gear surface comprising a second plurality of teeth that extend along the second curved surface about 180°.

6. The medical device of claim 1, wherein the drive gear includes a plurality of slots separated by a plurality of ribs extending laterally relative to the longitudinal axis, and wherein the first gear end comprises a first plurality of teeth and the second gear end comprises a second plurality of teeth, the first and the second teeth projecting substantially perpendicular to the longitudinal axis when engaged within the lateral slots.

7. A medical device comprising:
   a drive gear comprising an elongated rack defining a longitudinal axis and having a longitudinal length, the drive gear further comprising a first gear surface and a second gear surface being opposed to the first gear surface;
   a plurality of first ribs laterally protruding away from the first gear surface of the elongate rack along the longitudinal length of the drive gear, wherein the plurality of first ribs define a first plurality of slots therebetween,
   a plurality of second ribs laterally protruding away from the second gear surface of the elongate rack along the longitudinal length of the drive gear, wherein the plurality of second ribs define a second plurality of slots therebetween;
   a first elongate arm comprising a first jaw member and a first gear end, the first gear end comprising a first plurality of teeth pivotally connected within the distal end of the housing at a first pivot point, wherein the first plurality of teeth are engaged with the plurality of the first slots of the drive gear;

a second elongate arm comprising a second jaw member and a second gear end, the second gear end comprising a second plurality of teeth pivotally connected within the distal end of the housing at a second pivot point, the second plurality of teeth engaged with the plurality of the second slots of the drive gear; and a housing comprising a proximal end, a distal end, and at least one opening extending between the proximal end and the distal end, wherein the housing receives the first and the second elongate arms within the at least one opening in a fully open configuration to entirely enclose the arms, and wherein the first and second elongate arms are rotated to a position distal to the housing in a closed configuration.

8. The medical device of claim 7, wherein the at least one opening of the housing defines a first opening extending longitudinally through the distal end of the housing and opening laterally away from the longitudinal axis, and wherein the at least one opening of the housing further defines a second opening extending longitudinally through the distal end of the housing and opening laterally away from the longitudinal axis, the second opening spaced opposite the first opening.

9. The medical device of claim 7, wherein the first jaw member and the second jaw member are disposed generally parallel to each other in the fully open configuration, and further wherein the first elongate member and the second elongate member in the fully open configuration are positioned proximal of the distal end of the housing.

10. The medical device of claim 6, wherein the plurality of the first teeth are oriented along a first face of the first gear end.

11. The medical device of claim 10, wherein the plurality of the second teeth are oriented about a second face of the second gear end, the second face being oppositely disposed to the first face of the first gear.

12. The medical device of claim 1, wherein the first elongate arm and the second elongate arm have a longitudinal length of at least 12.7 millimeters and the overall diameter of the device is less than or equal to 20 Fr.

13. A method for grasping an object comprising the steps of:

providing a medical device comprising, a first elongate arm disposed within a housing and comprising a first jaw member and a first gear end, the first gear end intermeshed with a drive gear at the distal end of the housing;

a second elongate arm disposed within the housing and comprising a second jaw member and a second gear end intermeshed with the drive gear at the distal end of the housing;

wherein the first elongate arm and the second elongate arm are each pivotable about the first gear end and the second gear end, respectively, and further wherein each of the first elongate arm and the second elongate arm is pivotable between a fully closed configuration and a fully open configuration;

advancing the medical device to a position adjacent the object with the first jaw member and the second jaw member in the fully open configuration entirely enclosed within the housing in a substantially parallel arrangement with the first and the second jaw members disposed proximally of the first and the second gear ends;

pulling the drive gear in a proximal direction so as to cause engagement of the drive gear with the first gear end and the second gear end;

rotating the first elongate arm in a clockwise direction about the first gear end from a bottom opening of the housing;

rotating the second elongate arm in a counterclockwise direction about the second gear end from a top opening of the housing; and closing the first and the second jaw members around the object, the first and second elongate arms being positioned distal to the housing during the closing step.

14. The method of claim 13, comprising the steps of:

further pulling the drive gear so as to cause further engagement of the drive gear with the first gear end and the second gear end; and rotating the first elongate arm in the clockwise direction and rotating the second elongate arm in the counterclockwise direction until the first and the second jaw members are positioned in a substantially parallel arrangement in the fully closed configuration.

15. The method of claim 14, wherein the first elongate arm and the second elongate arm are disposed distal of the distal end of the housing in the fully closed configuration.

16. The method of claim 15, further comprising the steps of:

pushing the drive gear in a distal direction; and rotating the first elongate member in a counterclockwise direction and the second elongate member in a clockwise direction so as to reconfigure the first jaw member and the second jaw member in the open configuration within the proximal end of the housing in the fully open configuration.

17. The step of claim 13, wherein the drive gear defines mutually perpendicular longitudinal, lateral and vertical axes, and wherein engagement of the drive gear with the first gear end comprises projecting a first plurality of teeth substantially vertically within a plurality of lateral slots of the drive gear.

18. The step of claim 13, wherein engagement of the drive gear with the second gear end comprises projecting a second plurality of teeth substantially vertically within a plurality of lateral slots of the drive gear.

19. The step of claim 13, further comprising the step of pulling the drive gear in a proximal direction until a stopper element prevents further rotational engagement of the drive gear with the first and the second gear ends.

20. The device of claim 1, wherein each of the first and second elongate arms rotate at least 180° between the first closed position and the second open position.

* * * * *